United States Patent [19]

Evans et al.

[11] Patent Number: 4,625,013

[45] Date of Patent: Nov. 25, 1986

[54] AROMATIC SULFOXY COMPOSITIONS AND METHOD FOR THEIR PREPARATION

[75] Inventors: Thomas L. Evans; Marsha M. Grade, both of Schenectady, N.Y.

[73] Assignee: General Electric Company, Schenectady, N.Y.

[21] Appl. No.: 684,392

[22] Filed: Dec. 20, 1984

[51] Int. Cl.$^4$ .................... C08G 73/10; C08G 75/30
[52] U.S. Cl. ................................... 528/172; 528/352
[58] Field of Search ................ 562/429, 432; 568/27; 528/172, 352

[56] References Cited

U.S. PATENT DOCUMENTS

| | | | |
|---|---|---|---|
| 3,022,320 | 2/1962 | Bennett et al. | 562/429 |
| 3,529,017 | 9/1970 | Izard et al. | 562/432 |
| 3,622,525 | 11/1971 | Miller | 562/429 |
| 3,812,159 | 5/1974 | Lubowitz | 562/429 |
| 3,878,240 | 4/1975 | Kuenzy | 562/429 |
| 4,275,240 | 6/1981 | Yamaguchi et al. | 562/429 |
| 4,287,366 | 9/1981 | Yamaguchi et al. | 562/429 |
| 4,329,496 | 5/1982 | Webb | 562/429 |

*Primary Examiner*—Lucille M. Phynes
*Attorney, Agent, or Firm*—William H. Pittman; James C. Davis, Jr.; James Magee, Jr.

[57] ABSTRACT

Aromatic sulfoxy tetracarboxylic acids, and their derivatives such as dianhydrides, bisimides and polyimides, are prepared by oxidizing the corresponding sulfides under relatively mild conditions, using oxidizing agents such as nitric acid, N-chlorosuccinimide, potassium persulfate and hydrogen peroxide. The polyimides may also be prepared by the reaction of the dianhydrides or certain bisimides with diamines.

6 Claims, No Drawings

AROMATIC SULFOXY COMPOSITIONS AND METHOD FOR THEIR PREPARATION

This invention relates to new aromatic sulfoxy compositions of matter and methods for their preparation. More particularly, it relates to aromatic sulfoxy polyimides and monomeric intermediates therefor.

Polyimides are a known class of compounds useful as engineering resins. They are particularly valuable by reason of their high thermal stability and solvent resistance. The polyetherimides, illustrated by the reaction products of diamines with bis(ether anhydrides) such as 2,2-bis[4-(3,4-dicarboxyphenoxy)phenyl]propane dianhydride ("bisphenol A dianhydride"), are particularly useful for this purpose because of their processability. Also known are polyimides prepared entirely or in part from sulfide dianhydrides such as bis(3,4-dicarboxyphenyl)sulfide dianhydride. However, interest continues in the development of new polyimides with high thermal stability and solvent resistance.

A principal object of the present invention, therefore, is to provide novel polyimides and monomeric precursors therefor.

A further object is to provide polyimides characterized by high thermal stability and solvent resistance.

A still further object is to provide novel aromatic sulfoxy compounds and a method for their preparation.

Other objects will in part be obvious and will in part appear hereinafter.

In one of its aspects, the present invention is directed to compositions comprising aromatic sulfoxy tetracarboxylic acids and their derivatives having at least one structural unit of the formula

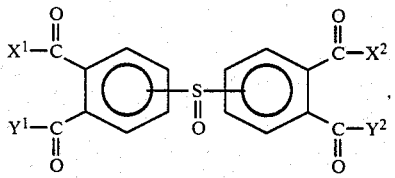

wherein:

$X^1$ and $X^2$ are both OH, $Y^1$ is OH or —NH— and $Y^2$ is OH or —NH—$R^1$—; or $X^1$ and $Y^1$ taken together and $X^2$ and $Y^2$ taken together are each O or $NR^2$; or $X^1$ and $Y^1$ taken together are

and $X^2$ and $Y^2$ taken together are

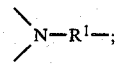

$R^1$ is a divalent hydrocarbon-based radical; and
$R^2$ is hydrogen, lower alkyl, phenyl or an electron-deficient radical.

As will be apparent from the above formula, the compositions of this invention include a wide variety of bis(phthalic acid)sulfoxide compounds. They are summarized in the following table.

| Compound | $X^1$ | $Y^1$ | $X^2$ | $Y^2$ |
|---|---|---|---|---|
| Tetracarboxylic acid | OH | OH | OH | OH |
| Dianhydride | (together) | O | (together) | O |
| Bisimide | (together) | $NR^2$ | (together) | $NR^2$ |
| Polyamic acid | OH | —NH— | OH | —NH—$R^1$— |
| Polyimide | (together) | ⟩N— | (together) | ⟩N—$R^1$— |

The $R^1$ value is a divalent hydrocarbon-based radical; this term includes hydrocarbon radicals as well as substituted and hetero radicals wherein the substituents or hetero atoms do not have a deleterious effect on the properties of the compound. Most often, $R^1$ is an aromatic hydrocarbon radical containing about 6–20 carbon atoms or a halogenated derivative thereof, an alkylene or cycloalkylene radical containing about 2–20 carbon atoms, or a bis-alkylenepoly(dialkylsiloxane) radical. The aromatic hydrocarbon radicals are preferred, and especially the m-phenylene, 4,4'-bis(phenylene)methane and 4,4'-bis(phenylene)ether radicals.

In compounds where the $R^2$ radical is present, it may be hydrogen, lower alkyl (i.e., alkyl of up to 7 carbon atoms) or phenyl. The preferred $R^2$ radicals are primary lower alkyl radicals, especially those containing up to 4 carbon atoms, and phenyl radicals. Especially preferred is the methyl radical.

The $R^2$ value may also be an electron-deficient radical. For the most part, suitable radicals of this type comprise aromatic hydrocarbon radicals containing one or more strongly electron-withdrawing substituents and heterocyclic radicals having aromatic character. Reference is made to copending, commonly assigned application Ser. No. 505,636, filed June 20, 1983, the disclosure of which is incorporated by reference herein.

Suitable aromatic hydrocarbon radicals include phenyl, naphthyl and the like containing such substituents as halo, nitro, keto, carbalkoxy, cyano and perfluoroalkyl. At least one of said substituents is preferably ortho or para to the free valence bond (i.e., the one attached to the imide nitrogen atom). The trifluoromethylphenyl radicals are particularly preferred within this subgenus.

Suitable heterocyclic radicals having aromatic character include those with 5- or 6-membered rings and aromatic unsaturation of the type existing in pyrrole and pyridine. These radicals preferably contain 1–3 and especially 1 or 2 hetero atoms of which at least one is nitrogen and the others, if present, are nitrogen or sulfur. They are usually unsubstituted but may be substituted, especially with electron-withdrawing substituents such as those previously enumerated. The free valence bond is preferably in the 2- or 4-position with respect to a hetero atom. If the ring contains more than one hetero atom and especially if it is 5-membered, the free valence bond is preferably attached to the single carbon atom between two of said hetero atoms.

Illustrative 5-membered heterocyclic radicals are pyrrolyl, 2-thiazolyl, 2-imidazolyl and 2-(1,3,4- thiadiazolyl). Illustrative 6-membered radicals are 2-pyridyl, 3-pyridyl, 4-pyridyl, 2-pyrimidyl, 2-pyrazyl, 2-(1,4-thiazolyl) and 2-(1,3-thiazolyl). Particularly preferred within this subgenus are the pyridyl radicals, especially 2-pyridyl and 4-pyridyl.

The carboxy moieties in the compositions of this invention may be attached to either aromatic ring in the 2,3- or 3,4-position with respect to the sulfoxy group. They are most often both attached in the 3,4-positions.

The dianhydride and bisimide compositions of this invention may be prepared by the oxidation, under relatively mild conditions, of a corresponding sulfide compound. Suitable oxidizing agents include nitric acid, hydrogen peroxide, potassium monopersulfate, percarboxylic acids, halosuccinimides, nitrogen tetroxide, halogens such as chlorine and bromine, iodobenzene dichloride, iodobenzene diacetate, sodium periodate and organic hypochlorites. Many of these oxidizing agents may also be used to oxidize the sulfides to the corresponding sulfones. Therefore, in order to obtain the sulfoxide it is frequently necessary to carefully control the reaction conditions, as by employing low temperatures, stoichiometric or less than stoichiometric amounts of the oxidizing agent, or heterogeneous reaction conditions with phase transfer catalysts.

A preferred oxidizing agent for the sulfide bisimide is nitric acid, which may be conveniently employed in the form of a mixture of fuming nitric acid and acetic anhydride. The stoichiometric molar ratio for complete oxidation of the sulfide to the sulfoxide is 2.5 moles of sulfide per mole of nitric acid. In order to minimize sulfone formation, it is usually preferred to employ a molar ratio of about 3.0-3.5:1 and to add the nitric acid mixture slowly to the sulfide at relatively low temperatures, typically between about −10° and about 10° C.

A second preferred oxidizing agent for the bisimide is N-chlorosuccinimide. Its oxidizing action is so mild that it may be used in stoichiometric amounts (i.e., a molar ratio of 1:1) and at temperatures generally in the range of about 30°-80° C. The reaction is normally effected in solution in a protonated organic solvent, typically an alkanol such as methanol. This method of oxidation may also be used on polyimides, as described hereinafter.

A third preferred oxidizing agent for the bisimide is potassium persulfate, which may be conveniently employed in the form of a mixture with potassium sulfate and potassium bisulfate. Such mixtures are commercially available under the trade name "Oxone". For persulfate oxidation, the bisimide may be dissolved in a suitable organic solvent, typically a chlorinated aliphatic hydrocarbon such as methylene chloride or chloroform, in combination with a phase transfer agent such as tetrabutylammonium bromide and the persulfate may be added in the form of an aqueous solution, typically at a temperature between about −20° and 0° C. By employing a relatively small amount of phase transfer catalyst, typically about 3-10 mole percent based on bisimide, it is possible to transfer the proper amount of persulfate into the organic phase for formation of the sulfoxide in high yield without close regulation of the amount of oxidizing agent used.

For production of the dianhydride compounds of this invention by oxidation of the corresponding sulfide dianhydrides, a preferred oxidizing agent is hydrogen peroxide, conveniently employed in combination with acetic anhydride so that the actual oxidizing species is acetyl peroxide. The oxidation may be conveniently effected by employing an approximately stoichiometric amount of hydrogen peroxide (i.e., equimolar amounts of the peroxide and the dianhydride) and temperatures within the range of about 10°-40° C.

The sulfoxy tetracarboxylic acids of this invention may be prepared by similar oxidation of the corresponding sulfide tetracarboxylic acids, or by hydrolysis of the sulfoxy bisimides or dianhydrides.

Following the oxidation reaction, the sulfoxy compound may be separated from unreacted sulfide and by-products such as sulfone and recovered by known methods which may include such conventional steps as column chromatography, fractional crystallization, distillation, solvent stripping and product precipitation.

The preparation of the sulfoxy bisimides and dianhydrides of the present invention is illustrated by the following examples. All percentages are by weight.

EXAMPLE 1

N-Chlorosuccinimide, 0.95 gram, was added at room temperature, with stirring, to a suspension of 2.5 grams of bis(3,4-dicarboxyphenyl)sulfide bis-N-methylimide in 100 ml. of methanol. The mixture was heated to 50° C. for 1 hour and then under reflux for 1 hour. The methanol was removed by vacuum stripping and the residue was dissolved in methylene chloride, washed twice with water and vacuum stripped. Upon recrystallization of the product from o-dichlorobenzene, there was obtained pure bis(3,4-dicarboxyphenyl)sulfoxide bis-N-methylimide. Its structure was confirmed by nuclear magnetic resonance and mass spectrometry and its purity by high pressure liquid-liquid chromatography. Its melting point was 241° C.

EXAMPLE 2

A solution of 500 mg. of bis(3,4-dicarboxyphenyl)sulfide bis-N-methylimide and 23 mg. of tetrabutylammonium bromide in 75 ml. of chloroform was cooled to −10° C. and a solution of 1.75 grams of "Oxone" in 10 ml. of water was added, with stirring. Stirring was continued for 18 hours as the mixture was allowed to warm slowly to room temperature. A 10% aqueous solution of sodium metabisulfate was then added to deactivate the oxidizing agent. The organic layer was separated and evaporated to dryness. The residue was shown by high pressure liquid-liquid chromatographic analysis to comprise 92.1% sulfoxide and 7.9% sulfone.

EXAMPLE 3

A solution of 1 gram of bis(3,4-carboxyphenyl)sulfide bis-N-methylimide in 6 ml. of acetic anhydride was cooled to 0° C. and a solution of 560 mg. of fuming nitric acid in 3 ml. of acetic anhydride was added dropwise, with stirring. After addition was complete, the mixture was allowed to warm slowly to room temperature as stirring was continued over 24 hours. It was then poured onto ice, diluted with water and neutralized with aqueous sodium carbonate solution. The aqueous mixture was extracted with methylene chloride and the extracts were dried over sodium sulfate and vacuum stripped. The residue was shown by high pressure liquid-liquid chromatography to comprise 25% sulfoxide and 75% unreacted sulfide.

EXAMPLE 4

A mixture of 5 grams (15 mmol.) of bis(3,4-dicarboxyphenyl)sulfide dianhydride, 2.06 grams (15 mmol.) of N-chlorosuccinimide and 250 ml. of methanol was heated to 50° C. with stirring for 1 hour and was then heated under reflux for one-half hour. It was evaporated to dryness under vacuum and the residue was washed with water, dried under vacuum and heated under reflux for 18 hours in acetic anhydride. The mixture was again evaporated to dryness, washed with anhydrous methanol and recrystallized from o-dichlorobenzene. A crystalline solid was obtained which was identified by field desorption mass spectrometry as bis(3,4-dicarboxyphenyl)sulfoxide dianhydride. It melted sharply at 220°–221° C.

EXAMPLE 5

To a suspension of 20 grams of bis(3,4-dicarboxyphenyl)sulfide dianhydride in 400 ml. of acetic anhydride was added with stirring, at room temperature, 6 ml. of 30% aqueous hydrogen peroxide. The mixture was allowed to stir overnight and was filtered. The solid residue, comprising 65% of the reaction mixture, was shown by analysis to consist of 65% sulfoxide and 35% unreacted sulfide. The filtrate was shown to comprise 93% sulfoxide and 7% sulfone.

The filtrate was evaporated to dryness, redissolved in acetic anhydride and heated to reflux to ensure complete ring closure. The mixture was vacuum stripped and the residue was recrystallized from o-dichlorobenzene. The resulting solid comprised 88.5% sulfoxide, 10.5% sulfone and 1.5% sulfide.

The above-described sulfoxides may be reacted with diamine in conventional manner to produce the polyimides of this invention and their polyamic acid precursors. Suitable polyimides include homopolyimides derived from the sulfoxy compounds alone and copolyimides derived from mixtures thereof with the corresponding derivatives of other tetracarboxylic acids such as pyromellitic acid, bis(3,4-dicarboxyphenyl)sulfone and 2,2-bis[4-(3,4-dicarboxyphenoxy)phenyl]propane. Examples of suitable diamines are ethylenediamine, propylenediamine, trimethylenediamine, diethylenetriamine, triethylenetetramine, heptamethylenediamine, octamethylenediamine, 2,11-dodecanediamine, 1,12-octadecanediamine, 3-methylheptamethylenediamine, 4,4-dimethylheptamethylenediamine, 4-methylnonamethylenediamine, 2,5-dimethylhexamethylenediamine, 2,2-dimethylpropylenediamine, N-methyl-bis(3-aminopropyl)amine, 3-methoxyhexamethylenediamine, 1,2-bis(3-aminopropoxy)ethane, bis(3-aminopropyl)sulfide, 1,4-cyclohexanediamine, bis-(4-aminocyclohexyl)methane, m-phenylenediamine, p-phenylenediamine, 2,4-diaminotoluene, 2,6-diaminotoluene, m-xylylenediamine, p-xylylenediamine, benzidine, 3,3'-dimethylbenzidine, 3,3'-dimethoxybenzidine, 1,5-diaminonaphthalene, bis(4-aminophenyl)methane, bis(4-aminophenyl)propane, 2,4-bis($\beta$-amino-t-butyl)toluene, bis(p-$\beta$-methylo-aminopentyl)benzene, 1,3-diamino-4-isopropylbenzene, bis(4-aminophenyl)sulfone, bis(4-aminophenyl)ether and 1,3-bis(3-aminopropyl)tetramethyldisiloxane. Mixtures of diamines may also be used. The preferred diamines are m-phenylenediamine, bis(4-aminophenyl)methane and bis(4-aminophenyl)ether.

In the reaction with diamines, about 0.95–1.05 moles of diamine is usually employed per mole of tetracarboxylic acid derivative. Particularly when the tetracarboxylic acid derivatives are dianhydrides, the reaction typically takes place in an aprotic solvent, often an aromatic solvent such as chlorobenzene, o-dichlorobenzene or a mixture of m-cresol and toluene. However, it is sometimes preferred to use aprotic solvents such as dimethylformamide, dimethylacetamide, dimethyl sulfoxide or N-methylpyrrolidone. In that event, it is frequently advisable to carry out the reaction in two stages in order to minimize reversibility which can result in decreased molecular weight of the polymer.

In the two-stage process, the first stage is the formation of a polyamic acid and the second stage is its imidization. The first stage is typically carried out at a temperature within the range of about 25°–100° C. and the second stage at about 180°–375° C. The second stage is normally carried out in the absence of solvents, although aromatic solvents such as those listed above may be used if desired.

It is also within the scope of the invention to include in the reaction mixture chain stopping agents, typically monofunctional aromatic amines such as aniline or monoanhydrides such as phthalic anhydride.

The polyimides of this invention may also be prepared by oxidation of the corresponding polythioetherimides under relatively mild conditions similar to those described hereinabove. For this purpose, a preferred oxidizing agent is N-chlorosuccinimide. Polythioetherimide oxidation is particularly effective and advantageous when the polymer is in the form of a film, since oxidation may be effected without dissolving or otherwise degrading the structural integrity of the polymer. Thus, the polymer film may be treated with a solution of the oxidizing agent and oxidized without dissolving or substantially swelling the film. This permits preparation of the sulfoxide polyimide by a relatively simple method, without the need for complex or difficult isolation or purification operations.

The preparation of the polyimides of this invention is illustrated by the following examples.

EXAMPLE 6

A mixture of 201.8 mg. (0.6 mmol.) of the mixture obtained from the filtrate of Example 5, 122.8 mg. (0.6 mmol.) of bis(4-aminophenyl)ether and 3 ml. of dimethylacetamide was stirred for 12 hours and then poured onto a glass plate. The plate was dried for 12 hours at 60° C. and then heated at 200° C. for 5 hours and under nitrogen at 300° C. for 5 hours. There was obtained a polyimide film having a glass transition temperature of 324° C.

EXAMPLE 7

A polythioetherimide was prepared by reacting bis(3,4-dicarboxyphenyl)sulfide dianhydride with an equimolar amount of bis(4-aminophenyl)ether in dimethylacetamide solution to form the polyamic acid, followed by casting a film of said polyamic acid and heating to form the polyimide film which had a glass transition temperature of 255° C. A sample of the film 0.04 mm. thick was added to a solution of 0.5 gram of N-chlorosuccinimide in 35 ml. of anhydrous methanol. The mixture was stirred at 50° C. for 18 hours, after which the film was removed, washed extensively with water and dried at 210° C. under nitrogen. The resulting surface-oxidized film had a glass transition temperature of 269° C.

The polyimides of this invention may be used for the formation of films, molding compounds, coatings and the like. Their use is of particular advantage where high thermal stability and solvent resistance are desired. Typical areas of utility are in automobile and aviation applications for decorative and protective purposes, as high temperature electrical insulators and dielectrics for capacitors, as coil and cable wrappings, for containers and container linings, in laminating structures for application as films to various heat-resistant or other types of materials, and as filled compositions where the fillers may be asbestos, mica, glass fiber or the like. Other uses include as binders for asbestos fibers, carbon fibers and other fibrous materials in making brake linings, and for formulation of molding compositions using fillers such as asbestos, glass fibers, talc, quartz, wood flour, finely divided carbon and silica. Other uses are similar to those described in U.S. Pat. No. 3,983,093, which is incorporated by reference. herein.

What is claimed is:

1. A polymer comprising structural units of the formula

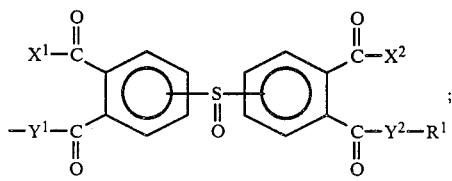

wherein:
$X^1$ and $X^2$ are both OH and $Y^1$ and $Y^2$ are both NH, or $X^1$ and $Y^1$ together are N and $X^2$ and $Y^2$ together and

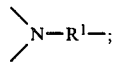

and
$R^1$ is an aromatic hydrocarbon radical containing about 6–20 carbon atoms or a halogenated derivative thereof, an alkylene or cycloalkylene radical containing about 2–20 carbon atoms, or a bisalkylenepoly(dialkylsiloxane) radical.

2. A composition according to claim 1 wherein the carboxy moieties are both attached in the 3,4-positions.

3. A composition according to claim 2 wherein $R^1$ is m-phenylene, 4,4'-bis(phenylene)methane or 4,4'-bis(phenylene)ether.

4. A method for preparing a polymer according to claim 1 which comprises oxidizing a corresponding sulfide polymer under relatively mild conditions.

5. A method according to claim 4 wherein the oxidation is effected by an approximately stoichiometric amount of N-chlorosuccinimide at a temperature within the range of about 30°–80° C.

6. A method according to claim 4 wherein $R^1$ is m-phenylene, 4,4'-bis(phenylene)methane or 4,4'-bis(phenylene)ether.

* * * * *